United States Patent [19]

Corr et al.

[11] 3,991,127

[45] Nov. 9, 1976

[54] PRODUCTION OF SATURATED ALIPHATIC ALCOHOLS

[75] Inventors: Hubert Corr; Erich Haarer, both of Ludwigshafen; Herwig Hoffmann, Frankenthal; Siegfried Winderl, Heidelberg, all of Germany

[73] Assignee: BASF Aktiengesellschaft, Ludwigshafen (Rhine), Germany

[22] Filed: Feb. 13, 1976

[21] Appl. No.: 657,926

Related U.S. Application Data

[63] Continuation of Ser. No. 92,222, Nov. 23, 1970, abandoned, which is a continuation-in-part of Ser. No. 711,859, March 11, 1968, abandoned.

[30] Foreign Application Priority Data

Mar. 18, 1967  Germany............................ 1277232

[52] U.S. Cl. .......................... 260/638 B; 252/457; 252/459; 252/463; 252/465; 252/466 B
[51] Int. Cl.² ........................................ C07C 29/14
[58] Field of Search ................................ 260/638 B

[56] References Cited

UNITED STATES PATENTS

| | | | |
|---|---|---|---|
| 1,738,971 | 12/1929 | Storch | 252/457 |
| 2,060,267 | 11/1936 | Toussaint | 260/638 B |
| 2,278,590 | 4/1942 | Ruthruff | 252/457 |
| 2,350,282 | 5/1944 | Lalande | 252/457 |
| 3,108,142 | 10/1963 | Reppe et al. | 252/466 B |
| 3,169,827 | 2/1965 | Rosset | 252/466 B |
| 3,193,348 | 7/1965 | Mooi | 252/466 B |
| 3,245,919 | 4/1966 | Gring et al. | 252/466 B |
| 3,260,769 | 7/1966 | Marshall | 260/682 |

*Primary Examiner*—Joseph E. Evans
*Attorney, Agent, or Firm*—Johnston, Keil, Thompson & Shurtleff

[57] ABSTRACT

Production of saturated aliphatic alcohols by continuously contacting olefinically unsaturated aliphatic aldehydes with hydrogen in a single stage at elevated temperature in the presence of catalysts containing metallic nickel, supported catalysts being used which contain 60 to 100% by weight of metallic nickel with reference to the metal content of the catalysts.

5 Claims, No Drawings

PRODUCTION OF SATURATED ALIPHATIC ALCOHOLS

This application is a continuation of our application Ser. No. 92,222, filed Nov. 23, 1970, now abandoned, the latter application being a continuation-in-part of application Ser. No. 711,859, filed Mar. 11, 1968, now abandoned.

The present invention relates to an improved process for the production of saturated aliphatic alcohols by hydrogenation of olefinically unsaturated aliphatic aldehydes in the presence of catalysts containing metallic nickel.

It is known from U.S. Pat. Specification No. 2,983,734 that saturated alcohols can be prepared by hydrogenation of unsaturated aldehydes in the presence of Raney nickel containing 0.5 to 3% by weight of chromium and in the presence of solvents. The process has the disadvantage that the catalyst used quickly becomes inactive so that it is unsuitable for continuous operation. According to another known process the hydrogenation of unsaturated aldehydes to the corresponding alcohols proceeds successfully in the presence of nickel catalysts having a nickel content of less than 50% by weight and in the presence of alcohols as solvents. Separation of the alcohol used however involves considerable expenditure. It is moreover known that aldehydes can be hydrogenated in two stages using catalysts which contain 5 to 30% by weight of copper, 3 to 20% by weight of nickel and 0 to 5% by weight of chromium. In another known process the aldehydes are hydrogenated in two stages in the presence of nickeliferous catalysts having a content of nickel which is preferably less than 15% by weight. Further methods for the hydrogenation of aldehydes are known from U.K. Patent Specifications Nos. 938,028 and 906,527 in which copper catalysts and nickel catalysts are used in separate zones. In another method described in U.K. Patent Specification No. 907,166 the first layer consists of a copper catalyst and the second layer consists of a copper-nickel catalyst, the ratio of copper to nickel being from 5:1 to 20:1. Finally, a process for the hydrogenation of unsaturated aldehydes is described in U.S. Patent Specification No. 3,288,866 which is carried out in two stages, a copper catalyst being used in the first stage and a catalyst containing palladium in the second stage. The said two-stage hydrogenation processes all have the disadvantage that they require great expenditure for instrumentation.

It is an object of the invention to provide an improved process in which unsaturated aliphatic aldehydes are hydrogenated in one stage into saturated aliphatic alcohols. Another object of the invention is to provide an improved process for the hydrogenation of unsaturated aliphatic aldehydes in which no additional solvent has to be used. A further object of the invention is to provide an improved process in which the catalysts used remain active over long periods.

In accordance with this invention, these and other objects and advantages are achieved by continuously contacting an olefinically unsaturated aliphatic aldehyde with hydrogen in one stage in the presence of catalysts containing metallic nickel at temperatures of 120° to 250° C, the improvement comprising using a supported catalyst which contains 60 to 100% by weight, with reference to its metal content, of metallic nickel.

Preferred olefinically unsaturated aliphatic aldehydes have three to twelve carbon atoms, particularly three to ten carbon atoms. They preferably contain in the molecule an olefinic double bond and a carbonyl group. Apart from the carbonyl group, the preferred starting materials have hydrocarbon structure. Examples of suitable starting materials are: acrolein, crotonaldehyde, 2-ethylhexen-(2)-al-(1), hexen-(2)-al-(1), decen-(2)-al-(1) and 2-methylpenten-(2)-al-(1). The process has particular industrial importance for the hydrogenation of 2-ethylhexen-(2)-al-(1).

Hydrogenation is advantageously carried out at temperatures of from 120° to 250° C, particularly at temperatures of from 140° to 200° C. Although it is possible to use atmospheric pressure, it is more advantageous to use superatmospheric pressure, for example up to 50 atmospheres, particularly up to 20 atmospheres. Hydrogenation is preferably carried out in the liquid phase. It is expedient to use 3 to 10 moles of hydrogen, particularly 5 to 8 moles of hydrogen, per mole of unsaturated aldehyde.

Hydrogenation proceeds in the presence of supported catalysts containing 60 to 100% by weight of metallic nickel, particularly 70 to 100% by weight of metallic nickel with reference to the metallic active material. It is an essential feature of the process according to the invention that the active metallic component of the supported catalyst should consist mainly of nickel. In addition to nickel, minor amounts of metals known as hydrogenation catalysts or activators may be present. Minor amounts of other metals may also be present provided they are inert. The catalysts may for example contain manganese, chromium, vanadium or copper, for example up to 40% by weight, particularly up to 30% by weight. It is advantageous to use non-acid substances such as aluminum oxide, carbon or non-acid silicates, for example magnesium silicate, as the carrier. In general a content of the said metals of 1 to 40% by weight with reference to the whole catalyst is adequate. Particularly good results are obtained with contents of 2 to 30% by weight. The percentages relate to the contents determined analytically in the finished catalysts, the metals being given as such, i.e. independently of the actual state of combination in which they are present. It is advantageous for the finished catalyst to have a pore size of 20 to 10,000, particularly 50 to 500 A and an internal surface area of 1 to 700 sq.m. per grams, particularly 50 to 300 sq. m. per gram.

The internal surface area and pore size are determined by the well-known BET method.

Suitable catalysts are prepared for example by precipitating aluminum hydroxide from aqueous solutions of aluminum salts such as aluminum sulfate or nitrate with caustic alkali solutions such as caustic soda solution or aqueous ammonia solution. The precipitate obtained is washed with water, dried at 100° to 125° C, pelleted and subsequently tempered for 4 to 8 hours at 400° to 800° C. The pellets thus obtained are impregnated at elevated temperature with aqueous solutions of easily decomposable salts, e.g. nitrates or oxalates of the above metals, dried at 100° to 125° C, and finally heated for 2 to 8 hours at temperatures of from 400° to 800° C. The pellets obtained contain the catalytically active metals in the form of their oxides. Determined by the BET method, their internal surface area is, for example, from 90 to 150 m²/g and their pore size, for example, 100 to 150 A. Before use the catalysts are reduced with hydrogen at temperatures of from 250° to 450° C.

The process according to the invention may be carried out for example by metering unsaturated aldehyde and hydrogen in the said ratio into the top of a tube which is charged with a catalyst having the said composition. If the unsaturated aldehyde is metered in in vapor phase, hydrogenation is carried out at atmospheric pressure; if the hydrogenation is carried out at superatmospheric pressure, the unsaturated aldehyde used is metered in in liquid form. The specified temperature is maintained in the tube during hydrogenation. The reaction product is separated from the hydrogen and the excess hydrogen can be metered in again at the top of the tube. The crude alcohol obtained can be isolated by fractional distillation.

Saturated aliphatic alcohols prepared according to this invention are suitable for the production of plasticizers, or they may be used without further processing as solvents.

The invention is illustrated by the following Examples. The parts specified in the following Examples are parts by weight unless otherwise stated. They bear the same relation to parts by volume as the kilogram to the liter.

EXAMPLE 1

Extrusions of aluminum oxide which contain 15% by weight of nickel, 5% by weight of copper and 1% by weight of manganese in the form of their oxides and having a internal surface of about 120 sq.m. per gram and a pore size of 100 to 150 A are charged into a high pressure vessel having a capacity of 500 parts by volume and reduced for 48 hours with hydrogen at atmospheric pressure at 350° C. Then 100 parts per hour of liquid 2-ethylhexen-(2)-al-(1) is passed with 140,000 parts by volume of hydrogen into the top of the high pressure vessel. A temperature of 150° C and a pressure of 20 atmospheres gauge are maintained. The reaction product is separated from hydrogen in a separator and analyzed by gas chromatography. The product contains 0.03% of 2-ethylhexen-(2)-al and 0.3% of 2-ethylhexanal as well as 2-ethylhexanol.

The boiling point is 184° to 185° C. The bromine number (consumption in mls of Kaufmann bromine solution per 100 mls of 2-ethylhexanol) is 25.

EXAMPLE 2

Extrusions of aluminum oxide containing 14% by weight of nickel, 0.8% by weight of manganese, 0.16% by weight of zinc, 1.6% by weight of copper, 0.5% by weight of silver, 1.4% by weight of iron and 0.7% by weight of chromium in the form of their oxides and having an internal surface area of about 120 m$^2$/g and a pore size of 100 to 150 A are charged into a high pressure vessel having a capacity of 500 parts by volume. The catalyst is reduced for 48 hours at 270° C at atmospheric pressure. Maintaining a temperature of 150° C and a pressure of 20 atmospheres gauge in the pressure vessel, 100 parts per hour of liquid 2-ethylhexen-(2)-al-(1) and 140,000 parts by volume per hour of hydrogen are metered in. The reaction mixture is separated from hydrogen in a separator and analyzed by gas chromatography. There is obtained 2-ethylhexanol having a boiling point of 184° to 185° C and containing 0.02% by weight of 2-ethylhexen-(2)-al-(1) and 0.2% by weight of 2-ethylhexanal. The bromine number is 18.

EXAMPLE 3

The procedure of Example 2 is adopted, except that the aluminum oxide extrusions contain 12.6% by weight of nickel, 0.1% by weight of cobalt, 0.1% by weight of manganese, 0.1% by weight of zinc, 3.2% by weight of copper, 0.1% by weight of silver and 0.3% by weight of chromium in the form of their oxides. The internal surface area is about 120 m$^2$/g and the pore size 100 to 150 A. 2-ethylhexanol is obtained having a boiling point of 184° to 185° C and containing 0.04% by weight of 2-ethylhexen-(2)-al-(1) and 0.4% by weight of 2-ethylhexanal. The bromine number is 35.

COMPARATIVE EXAMPLE

The procedure of Example 2 is adopted, except that the catalyst consists of silicic acid extrusions containing 15% by weight of nickel, 5% by weight of copper and 1% by weight of manganese in the form of their oxides. 2-ethylhexanol is obtained having a boiling point of 184° to 185° C and containing 0.2% by weight of 2-ethylhexen-(2)-al-(1) and 2% by weight of 2-ethylhexanal. The bromine number is 200.

EXAMPLE 4

The procedure of Example 1 is adopted, except that there are metered per hour into the pressure vessel 100 parts of liquid 2-methylpenten-(2)-al-(1) and 100,000 parts of hydrogen. In the pressure vessel a temperature of 170° C and a pressure of 50 atmospheres gauge are maintained. After separation of the hydrogen, the reaction product contains, in addition to 2-methylpentanol, 0.2% by weight of 2-methylpenten-(2)-al-(1) and 0.3% by weight of 2-methylpentanal. The bromine number is 20.

We claim:

1. A process for the production of alkanols having three to ten carbon atoms by continuously contacting an alkenal having three to ten carbon atoms with hydrogen in a molar ratio of 1:3 to 1:10 at a temperature of 120° to 250° C and at a pressure from atmospheric pressure to 50 atmospheres in the presence of a supported catalytically active metal hydrogenation catalyst, wherein the improvement consists of using a supported catalytically active metal hydrogenation catalyst which contains, excluding the support, 60 to 100% by weight of nickel with reference to the catalytically active metal content and which may contain, in addition to nickel, up to 40% by weight, with reference to the catalytically active metal content, of a metal or metals selected from the group consisting of manganese, chromium, vanadium and copper, the percentages of the catalytically active metals being given independently to their actual state of combination, and said support being aluminum oxide.

2. A process as claimed in claim 1 wherein said alkenal is 2-ethylhexen-(2)-al-(1) or 2-methylpenten-(2)-al-(1).

3. A process as claimed in claim 1 wherein said temperature is in the range of 140° to 200° C.

4. A process as claimed in claim 1 wherein hydrogenation is carried out in the liquid phase.

5. A process as claimed in claim 1 wherein 5 to 8 moles of hydrogen is used for each mole of alkenal.

* * * * *